United States Patent [19]

Zweig et al.

[11] Patent Number: 4,871,831

[45] Date of Patent: Oct. 3, 1989

[54] COMPLETE ETHER CAPPING OF OLIGOMERIC POLYPHENOLS

[75] Inventors: Andrew M. Zweig, Schaumburg; Jeffrey P. Conrad, Chicago, both of Ill.

[73] Assignee: Allied-Signal Inc., Morristown, N.J.

[21] Appl. No.: 126,314

[22] Filed: Nov. 30, 1987

[51] Int. Cl.$^4$ ............................................. C08G 63/38
[52] U.S. Cl. .................................... 528/205; 528/219; 528/392; 528/396; 528/397; 525/132; 525/502; 525/504; 525/505; 525/534; 525/539; 525/934; 524/115; 524/155; 524/430
[58] Field of Search ............... 528/205, 219, 392, 396, 528/397; 525/132, 502, 504, 505, 534, 539, 934; 524/115, 155, 430

[56] References Cited

U.S. PATENT DOCUMENTS

| | | | |
|---|---|---|---|
| 3,625,874 | 12/1971 | Cottman et al. | 260/5 |
| 4,116,936 | 9/1978 | Steiner | 526/286 |
| 4,707,558 | 11/1987 | Wang et al. | 568/23 |

Primary Examiner—John Kight
Assistant Examiner—Acquah, S. A.
Attorney, Agent, or Firm—Harold N. Wells; Thomas K. McBride; Eugene I. Snyder

[57] ABSTRACT

A method is presented to prepare totally functionalized ether-capped oligomeric polyphenols without molecular weight fractionation. The products generally are very low in inorganic salts and are characterized by the absence of volatiles leading to void formation in their subsequent curing. The success of the method rests upon conducting the reaction under totally homogeneous conditions throughout.

30 Claims, No Drawings

COMPLETE ETHER CAPPING OF OLIGOMERIC POLYPHENOLS

The subject matter of this application is directed toward the preparation of resins used in the manufacture of reinforced plastics. The resins (binders) of particular interest here are those used on the preparation of composites formed from fibers embedded in a polymer resin matrix, especially those resins used in the preparation of circuit board laminates where the reinforcing material is glass or quartz fiber.

To overcome some mechanical and structural limitations of plastics it has become relatively commonplace to reinforce them with other components. Composites formed of various fibers embedded in a polymer resin matrix are especially useful and susceptible to enormous variation depending upon the nature of the fiber used, how the fiber is utilized, and the matrix or binder for the fibers. Materials which have been used as fibers include glass, quartz, oriented polymers such as the aramids (Kevlar TM), graphite and boron. Whatever their composition such fibers can be used as chopped or continuous filaments, and when used as continuous filaments they can all be unidirectional or woven into a fabric. The matrix can be, for example, a polyester, epoxy, polyimide, polyetherketone or polyetherimide resin as either a thermoset or thermoplastic material. The uses for such composites range from airframes to tennis rackets and from boat hulls to rocket motor casings.

A particular area of composite application is that of printed circuit boards, especially multilayer circuit boards, for mounting electronic components. The use of glass fabric as the reinforcing material has become more-or-less standard and epoxy resins are most often used as the matrix. For the fiber to exert a reinforcing action it is necessary that the fibers be completely coated with resin, and to achieve this the glass fiber often is surface treated to provide sites for chemical bonding to the resin or to its precursor or for otherwise improved adhesion to the matrix material.

Multilayer circuit boards are laminates with alternating layers of composite and etched copper sheet. A brief discussion of their manufacture will aid in appreciating the properties requisite for such boards. A woven glass fabric is first impregnated with resin by dipping the cloth in a resin solution, often referred to as the varnish solution, in what is called the A-stage. Solvent is then removed to afford a glass cloth reinforced resin, or prepreg, in what is called the B-stage. In some cases the resin in the prepreg may be partially cured, in other cases uncured, but in all cases the prepreg is a non-tacky, readily handled rigid sheet of glass cloth embedded in and coated with a resin. The finished circuit board is prepared by laminating alternating layers of prepreg and etched copper foil under conditions of temperature and pressure where resin is cured, i.e., further polymerized and crosslinked to a final infusible, insoluble stage (C-stage).

From the above brief description some necessary and desirable characteristics of the resin may be readily discerned. The circuit board will be subjected to soldering temperatures and may be operated at an elevated temperature, or experience cyclic locally elevated temperatures because of local power generation, and thus the thermal coefficient of expansion of the resin should approximate that of glass to ensure continued dimensional stability and resistance to heat distortion. The resin should have a high solubility in the varnish solution to ensure high resin loading. The varnish solution should have a sufficiently low viscosity for even coating but not too low a viscosity as to run off the fibers. It is necessary that the prepreg not be tacky so that it can be readily handled and stored. The resin is desirably non-crystalline for enhanced solubility in the varnish solution and for good film forming properties in the prepreg. The resin should have adequate flow at the C-stage so as to make void-free laminated bonds, with the curing temperature somewhat higher than the glass transition temperature ($T_g$) of the resin to afford a wider processing "window." The resin also should be chemically resistant to a corrosive environment and to water vapor. To ensure that the discrete electrical components on a circuit board interact only via the etched path on the copper foil, it is desirable that the matrix have a low dielectric constant and high resistance.

Ether-capped polyphenols often are used as resins in circuit board laminates. Exemplary of such polyphenols are those described in U.S. Pat. No. 4,116,936, e.g., bisphenol-A,

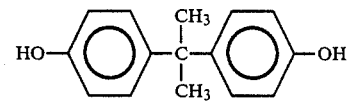

and from low molecular weight oligomers of the above. Also exemplary of such polyphenols are those of Ser. No. 947,007, which are polyphenolic oligomeric condensation products of dialdehydes and phenols, such as

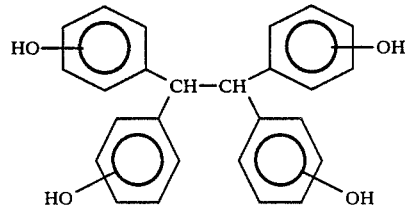

and related oligomers. The polyphenols cited above are themselves not used as resins, but their unsaturated ethers, such as the allyl and vinylbenzyl ethers, have been used because of their relative ease of polymerization (curing).

Any method to ether-cap polyphenols must meet several criteria, some of which arise from their use in laminated circuit boards. The chief requirement is that complete functionalization of the phenolic hydroxyl groups is achieved, by which we mean that desirably 100%, but at least 90%, of these hydroxyl groups are converted to ethers. Incomplete functionalization leads to a cured resin which exhibits excessive water absorption and degraded dielectric properties. Another requirement is that there be no molecular weight fractionation in the isolation and separation of the oligomeric ether-capped polyphenols. The presence of the lower molecular weight oligomers tends to ensure a high cross-linking density which affords a cured resin with a lower temperature coefficient of expansion as well as a lower dielectric constant. Yet another requirement is that there be little or no entrapment or incorporation of ionic materials in the product, for the presence of such materials, generally in the form of salts, has a severe deleterious effect on the dielectric performance of the cured resins. Finally, one requires that the ether-capped polyphenols be formed in high yields so as to minimize cost.

In a prior art method of U.S. Pat. No. 4,116,936 the patentee prepared the vinylbenzyl ether of polyphenols by adding a methanolic potassium hydroxide solution to an acetone solution of the polyphenol and vinylbenzyl chloride at reflux followed by filtration (to remove potassium chloride), evaporation of solvent, and precipitation of the residual oil into methanol. Although the method works well with monomers, it is less satisfactory when used with low molecular weight oligomers. For example, the patentee in his Example III shows that the method affords the ether-capped oligomeric polyphenols in low yield. That the patentee needed to use chromatography to remove phenolic material also demonstrates that the reaction proceeded with incomplete functionalization of the polyphenol.

When we employed the method with somewhat higher molecular weight oligomeric polyphenols we encountered a multiplicity of difficulties. The reaction invariably led to incomplete functionalization. Solids from the oily reaction product were not consistently obtained, and the reaction product itself generally was obtained in low yield (under 50%). The reaction product contained inorganic salts which were extremely difficult to remove, even with repeated filtration. We also observed that fractionation of the oily product occurred by phase separation of the higher molecular weight materials leaving the lower oligomers is solution to afford a product with lower cross-linking density and poorer thermal properties. We also observed that vinylbenzylmethyl ether was entrapped in the oil leading to bubbles (void formation) upon curing the resins. Finally, this method resulted in inefficient use of vinylbenzyl chloride, and expensive commodity.

Many of the foregoing difficulties seemed to be associated with phase separation of the organic product during reaction, a separation which led to product fractionation by molecular weight and entrapment of other products and/or reactants in the viscous oil which separated. Several variations on a preparative theme were explored without success, making it increasingly clear that a radical departure from the prior art method would be necessary to overcome the deficiencies in the prior art method. In particular, it appeared critical to maintain all organic components of the reaction mixture in solution during reaction in order to avoid the aforementioned problems. Continued research led to a synthesis where base-catalyzed reaction between oligomeric polyphenols and, for example, vinylbenzyl chloride was performed in a polar aprotic solvent with subsequent processing employing a low boiling non-polar, water-immiscible solvent. The method of ether-capping polyphenols to be described, which is our invention, has the advantage of completely capping the phenolic hydroxyl groups. It also has the advantage of retaining the lower molecular weight oligomeric resins, thereby leading to a higher cross-linking density in the cured resin with its associated beneficial effects manifested as a lower thermal expansion and a lower dielectric constant. Our invention also affords the ether-capped polyphenol in quite yield and with a content of ionic material under about 50 ppm. A further advantage of our invention is that there is no entrapment of materials analogous to vinylbenzyl methyl ether, i.e., volatile but not low-boiling compounds which cause void formation in subsequent thermal curing. And because our method utilizes phenolic hydroxylreactive halides efficiently it is cost effective.

SUMMARY OF THE INVENTION

The purpose of this invention is to convert oligomeric polyphenols to their ethers in high yield, without molecular weight selection or fractionation, and with complete, or virtually complete, functionalization of the phenolic hydroxyl groups. An embodiment comprises reacting the polyphenol and appropriate unsaturated halides, or a mixture of saturated and unsaturated halides, in a polar aprotic solvent in which all organic reactants and organic reaction products remain soluble with subsequent removal of the formed salts and the polar aprotic solvent by dilution with a water immiscible organic solvent and extensive water washing. In a more specific embodiment the polar aprotic solvent is N-methylpyrrolidone. In yet another embodiment the halide is a vinylbenzyl halide in whole or in part. In a further embodiment the water immiscible organic solvent is toluene. Other embodiments will appear clear from the following.

DESCRIPTION OF THE INVENTION

This invention is based on the discovery resulting from the experience of numerous failures, that complete ether capping of oligomeric polyphenols in high yield without molecular weight fractionation, without entrapment of ionics and of materials volatilizing at the curing temperature of the resulting resin, can be achieved if the reaction is conducted under homogeneous conditions with respect to all organic components at all stages of product formation. This later object can be achieved where the reaction is performed in a polar aprotic solvent; subsequent processing using a water immiscible organic solvent affords a highly effective process of great generality and obviates virtually all the disadvantages of the prior art methods.

The polyphenols which are used in the practice of this invention are polyhydric phenols having molecular weight, from about 200 up to approximately 10,000. Because the polyphenols which are ether-capped in the practice of this invention generally are oligomeric products of some kind of condensation reaction, there usually will be a spectrum of molecular weight products present, i.e., the polyphenols will be a mixture of oligomers. Normally such an oligomeric mixture will have a weight-average molecular weight no greater than about 5,000, and even more frequently it will not exceed about 3,000.

Exemplary of such polyphenols are the oligomeric condensation products of dialdehydes and phenols previously mentioned. Also exemplary of such polyphenols, and illustrative of yet another class of polyphenols, are phenol-polyolefin reaction products as described in U.S. Pat. No. 3,625,874. These are essentially Friedel-Craft condensation products where the phenol is alkylated preferentially at the ortho- or para-position relative to the hydroxyl group, and condensation products with cyclic polyolefins such as dicyclopentadiene which are subsequently ether-capped with unsaturated moieties find use in circuit board laminates. Another class illustrative of the polyphenols used in this invention are polyphenylene oxides. It needs to be emphasized that the polyphenols mentioned above are merely exemplary and illustrative of those which can be used in the practice of our invention, but the invention certainly is not limited only to those polyphenols stated above.

What is desired is to ether-cap all, or virtually all, of the phenolic hydroxyl groups where a substantial portion, generally 50% or more, of the ether-capping groups are unsaturated. Ether-capping with an unsaturated group affords a resin which can be readily cured at somewhat elevated temperatures to afford an extensively cross-linked product suitable in the preparation of laminated circuit boards. Ether-capping is most readily done by reacting the polyphenols with phenolic-reactive halides which are unsaturated halides, at least in part. Such unsaturated halides are either allylic halides or styrene-like benzyl chlorides and may be described by the general formula, $$CH_2=\overset{R}{\underset{|}{C}}-Z-Hal,$$

where Hal is a halogen, generally chlorine, although bromine and iodine may be used, but less conveniently; R is hydrogen or a lower alkyl group containing from 1 through about 6 carbon atoms, and Z is $CH_2$, benzyl,

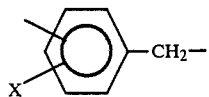

or the biphenyl analog of benzyl,

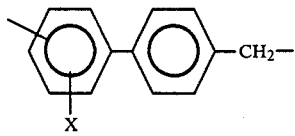

where X is hydrogen, a halogen, or a trifluoromethyl group. The vinylbenzyl moiety (R=H, Z=benzyl) is particularly recommended. Where Z=$CH_2$ the allyl moiety has from 3 up to about 9 carbon atoms.

As stated previously, the final cured resin arises from polymerization of the unsaturated sites in the ether moiety. It has been found that, at least in some instances, a sufficiently high cross-linking density is achieved when as little as about 40% of the ether moieties arising from phenolic-reactive halides are unsaturated, although generally half or more of such moieties are unsaturated. The remainder of the phenolic-reactive halides may be saturated primary alkyl halides containing up to 10 carbons, although the lower alkyl groups containing from 1 to 6 carbon atoms are preferred, or a benzyl group, since polymerization (curing) does not occur via the aromatic ring.

Where both unsaturated and saturated phenolic-reactive halides are used, i.e., where part of the ether-capped polyphenols have an unsaturated ether moiety and the remainder have a saturated moiety, the preferred mode of preparation is to first react the polyphenol with the unsaturated halide followed by reaction of the resulting partially ether-capped polyphenol with a large excess of the saturated phenolic-reactive halide. Although ether capping may be done by reacting a mixture of both unsaturated and saturated halides with the polyphenol, this variant is less desirable because of the concurrent formation of materials which volatilize during thermal curing of the formed resin.

Since the reaction between the unsaturated halide and the polyphenol is essentially quantitative, an amount of the unsaturated halide corresponding to the desired percentage of the stoichiometric quantity of unsaturated ether is used where unsaturated groups are only a portion of the ether moieties. For example, if the final product contains desirably 70% of vinylbenzyl ether and 30% of the n-propyl ether, the initial reaction is between the polyphenol and an amount of, for example, vinylbenzyl chloride corresponding to 70% of the stoichiometric amount necessary to react with all of the hydroxyls in the polyphenol. If one defines an equivalent of phenolic-reactive halide as that amount containing the number of molar proportions of halide necessary to completely react with all of the phenolic hydroxyl groups in one molar proportion of polyphenols, the foregoing can be restated that 0.7 equivalents of the unsaturated halide are first reacted with the polyphenols. After reaction with the unsaturated halide is complete, additional base and the saturated reactive halide is added to react with the remaining phenolic hydroxyl groups of the partially etherified polyphenol. At least one equivalent of total phenolic-reactive halide must be used, but most often a large excess of the saturated halide is used to ensure complete functionalization, that is, reaction of at least 90% of all hydroxyl groups in the polyphenol, more desirably at least 95%, and most desirably substantially all, or 100%, of all hydroxyl groups. Such complete functionalization is desirable to optimize dielectric properties. However, where the halide is expensive, e.g., where only an unsaturated halide is utilized, a smaller excess is desirable, although for complete functionalization at least 5 percent excess, or 1.05 equivalents, is recommended. In general, at least 1.05 equivalents of total phenolic-reactive halides are used in the practice of this invention, although more usually at least 1.10 equivalents are used, and where the halide is relatively inexpensive an even greater number of equivalents are used to ensure complete functionalization.

It is necessary that the reaction be conducted in a solvent in which all of the reactants and organic products are soluble throughout the course of the reaction, that is, the reaction proceeds under homogeneous conditions with respect to all organic components of the mixture from its beginning to end. It has been found that precipitation of at least a portion of the inorganic salts formed in the reaction may occur, but that this is not deleterious so long as all organic reactants and products remain in solution. Polar aprotic solvents as a class have been found quite desirable in maintaining homogeneity of the reaction mixture with respect to its organic reactants and products, and the particular member of the class used will depend principally on the solubility of the polyphenol in that member. Examples of polar aprotic solvents which may be used, subject to the solubility of the desired polyphenol in such solvent, include N-methylpyrrolidone, dimethylformamide, dimethylacetamide, hexamethylphosphoramide, and dimethylsulfoxide.

The reaction between the phenolic-reactive halides and the phenolic hydroxyl moieties occurs in the presence of a strong base such as the alkali metal and quaternary ammonium hydroxides, with the alkali metal alkoxides being quite desirable alternatives. When alkali metal hydroxides are utilized their relative insolubility in the polar aprotic solvents used in the practice of this invention necessitate their prior solution in, for example, an alcohol. Under these circumstances very concentrated solutions of the hydroxide and alcohol, for example, up to about 9 molal, are used to introduce the minimum amount of alcohol into the reaction medium. Because of its greater solubility in alcohols, especially the lower alcohols such as methanol, potassium hydroxide is the favored alkali metal hydroxide and methanol is the favored alcohol.

It also has been found that trace amounts of water may be quite deleterious to the progress of this reaction. Consequently, conducting the reaction in the presence of drying agents, such as molecular sieves, affords substantial benefit. Because water is introduced through the use of alkali metal hydroxides, both as water absorbed by the hydroxide and water formed in the course of the reaction, it has been found quite advantageous to substitute alkali metal alkoxides as the base. So, for example, the use of sodium methoxide, sodium ethoxide, sodium propoxide, sodium butoxide, and so on, as well as the analogous potassium and lithium salts are a desirable variant in our invention.

Whatever base is used, it is used in an approximately stoichiometric amount relative to the phenolic-reactive halides. Where the halides are added in portions, i.e., an unsaturated halide first added followed by a saturated halide, the base also is added in portions and in a stoichiometric quantity relative to each portion of reactive halide used. A stoichiometric amount of base is required for complete reaction, especially where only a small excess of reactive halide is used, but a greater amount may be used although with no substantial benefit. Where a large excess of halide is used somewhat less than a stoichiometric quantity of base may be used, although this is not recommended.

The reaction is conducted at a temperature whose maximum is dictated largely by the temperature at which polymerization of the unsaturated halide begins. For example, if vinylbenzyl chloride is the phenolic-reactive halide a reaction temperature of no more than 60° C. is used since there is substantial polymerization of vinylbenzyl chloride above such temperatures. The reaction temperature generally is at least 40°, and more usually it is at least 50° C. Reaction times at a temperature near 60° are about 4 hours where vinylbenzyl chloride is used, and from 2 to 4 hours where a saturated phenolic-reactive halide is utilized.

When the reaction is complete the reaction product mixture is diluted with a water immiscible nonpolar solvent whose boiling point is under about 40° C. at 5 millimeter pressure so that the solvent may be conveniently stripped at a later time. In addition to the foregoing restrictions, the nonpolar solvent also must dissolve all of the oligomeric ether-capped polyphenols and should be one such that the distribution coefficient of the polar aprotic solvent between the water immiscible solvent and water is highly biased toward the latter. That is, the polar aprotic solvent should have a much higher solubility in water than in the nonpolar water immiscible organic solvent. Examples of suitable solvents include aromatic compounds such as benzene and its alkylated analogs, especially toluene, xylene, propylbenzene, ethylbenzene, and so forth, and the haloalkanes and haloalkenes, especially the chloro compounds such as methylene chloride, chloroform, carbon tetrachloride, trichloroethane, tetrachloroethane, tetrachloroethylene, and so forth. Chlorinated hydrocarbons sometimes have the disadvantage of being too good a solvent for the polar aprotic solvent so that in subsequent water washings the polar aprotic solvent is removed only incompletely or with difficulty. The amount of the water immiscible organic solvent used is not critical to the success of this invention, but generally it has been convenient to add an amount roughly equal to that of the aprotic polar solvent, with larger amounts of such solvent usable but without obvious benefit or detriment. This amount ordinarily is sufficient to precipitate the inorganic salts without insolubilizing the ether-capped oligomeric polyphenols.

Upon addition of the water immiscible organic nonpolar solvent to the reaction mixture the salts generally immediately precipitate. It is often advantageous to remove such salts at this phase such as by filtration or centrifugation followed by extensive water washing of the filtrate. However convenient this variant may be it is not necessary to the success of this invention, and an acceptable alternative is to wash the entire mass with water so as to remove the inorganic salts and the dipolar aprotic solvent simultaneously.

As previously stated, the organic phase is extensively washed with water to remove all the water soluble components. The organic phase which is recovered is a salt-free solution of totally functionalized ether-capped oligomeric polyphenols essentially free of the dipolar aprotic solvent. By "salt free" is meant that inorganic salts are present to the extent of less than 50 ppm, and often less than 30 ppm. The resulting solution of totally functionalized ether-capped oligomeric polyphenols then may be concentrated by evaporation of the organic solvent (stripping) to give a concentrated solution of ether-capped polyphenols which can be used directly in a prepregging operation. Alternatively, all of the solvent may be removed by evaporation, especially under reduced pressure, to afford an unfractionated oligomeric mixture of ethers.

The examples which follow are only illustrative of specific embodiments of our invention. Other embodiments are well within the abilities of one skilled in the art and are intended to be included in our invention.

Tetraphenol ethane (TPE) was purchased from Borden Chemical and showed an average molecular weight by gel permeation chromatography corresponding to an oligomer with 7 phenolic groups per molecule. Vinylbenzyl chloride (VBC) was used as a mixture of para- and meta-isomers.

EXAMPLE I 1,1,2,2-Tetrakis(m,p-vinylbenzyloxy)ethane and oligomers thereof by the prior art procedure (U.S. Pat. No. 4,116,936). In this example, 100 grams (0.142 mole) of TPE ($M_n=274$, $M_w=711$) and 166.54 grams (1.091 moles) of vinyl benzyl chloride (60/40 meta/para isomer ratio) were dissolved in 250 milliliters of acetone in a three neck-round bottom flask which was equipped with a condenser, addition funnel, thermometer, mechanical stirrer, and nitrogen purge. The reaction mixture was then heated to reflux (65°-70° C. temperature) for a period of 1 hour, following which a solution of 67.5 grams (1.202 moles) of potassium hydroxide in 150 milliliters of methanol was added to the warm reaction mixture over an interval of 30 minutes with continuous stirring. The reaction mixture was maintained at reflux for a period of 1 hour, thereafter diluted with 400 milliliters of acetone and was then stirred at ambient temperature for a period of 24 hours. The reaction mixture was recovered, dried over magnesium sulfate, filtered, and concentrated under vacuum. The oil was then taken up in an equal volume of acetone and precipitated from the acetone solution by the addition of methanol. The resulting solid was vacuum dried at ambient temperature for a period of 24 hours to yield 87.0 grams (40%) of a yellow crystalline material having a melting point of 52° C., $M_n$ (number-average molecular weight) of 1.088K, $M_w$ (weight-average molecular weight) of 5.080K and R (dispersity index) of 4.67. The large shift to a very high $M_w$ indicates fractionation of the product has occurred and the low molecular weight oligomers have been lost resulting in a lower crosslinking density and poorer thermal performance. The infrared spectrum of the product indicates that hydroxyl functionality remains in the resin which led to increased water absorption and poorer dielectric performance of the cured material. The resin still contained inorganic salts which are also deleterious to dielectric performance.

If the product is not precipitated as described by Steiner but washed as described in this disclosure, other difficulties are encountered. Yields are improved but large amounts of semi-volatile impurities are trapped in the resin. Diacetone alcohol, the aldol self condensation product of acetone, and vinylbenzyl methyl ether (VBME), the base catalyzed product of VBC and methanol, are produced in large quantities as side products of the Steiner method when applied to highly functionalized oligomeric systems. The presence of these compounds degrades the performance of the cured resin by producing voids on thermal curing and by acting to elasticize the polymer matrix.

EXAMPLE II 1,1,2,2-Tetrakis(m,p-vinylbenzyloxy) ethane and oligomers thereof by a modified Steiner procedure. To a 5 L three-necked round bottom flask fitted with a mechanical stirring shaft and charged with 2.8 L of methanol, 0.62 g of BHT, a hindered phenolic radical inhibitor, and 200.00 g (0.283 mol) of TPE was added 80.82 g (2.021 mol) of sodium hydroxide. A reflux condenser, a pressure equalizing dropping funnel and a heating mantle were brought into place. The vessel was flushed with nitrogen and then kept under positive nitrogen pressure by a mineral oil bubbler. The mixture was brought to reflux and upon dissolution of the sodium hydroxide 308.37 g (2.021 mol) of VBC was added dropwise over 35 minutes. Reflux was continued an additional four hours. A yellow/red oily product precipitated over the course of the reaction. The mixture was allowed to cool by immersion in an ice bath and 140 mL of water was added to quench the reaction. The supernatant was decanted and 200 mL of fresh methanol was added to rinse the product. The rinsed product was dissolved in 3.2 L of acetone and the sodium chloride allowed to settle out. The solution was filtered, dried over MgSO$_4$ and filtered again. The solvent was removed by rotary evaporation at 40° C. at 3 torr; 288 g (67%) of a dark red resin were obtained. The infrared spectrum of the product indicated that residual hydroxyl functionality remain in the resins which led to increased water absorption and poorer dielectric performance of the cured material. The resins also contained considerable amounts of inorganic salts which were not removed by repeated filtration. Additionally, the resins contained vinylbenzylmethyl ether as a side product which was not volatile enough to be removed by rotary evaporation. Upon thermal curing void formation and degraded performance of the cured resin was observed.

EXAMPLE III

Styrene/propyl Terminated Tetraphenol Ethane (90% vinylbenzyl, 30% propyl). To a 5 L three-necked round bottom flask fitted with a mechanical stirring shaft and charged with 1670 mL of 1-methyl-2-pyrrolidinone, 3.30 g of BHT, a hindered phenolic radical inhibitor and 353.00 g (0.500 mol) of TPE ($M_n$=274; $M_w$=711) were added 373.89 g (2.45 mol) of VBC. A reflux condenser, pressure equalizing dropping funnel and a heated water bath were brought into place. The flask was flushed with nitrogen and then kept under positive nitrogen pressure by a mineral oil bubbler. The temperature was brought to 60° C. A solution of 160.25 g (2.50 mol) KOH in 360 mL of methanol was placed in the addition funnel and added over 30 minutes. The temperature was maintained at 60° C. by addition of ice to the water bath. The reaction was allowed to proceed an additional 3.5 hours. 172.20 g (1.40 mol) of 1-bromopropane was then added to the flask. A second solution of 68.68 g (1.07 mol) of KOH in 150 mL of methanol was added via the addition funnel over 30 minutes. Temperature was maintained at 60° C. for an additional 2.5 hours. The flask was then allowed to cool and 2.5 L of methylene chloride was added causing salts to precipitate out of the reaction mixture. 6.25 L of water was then added and the solution washed in a separatory funnel by rapid stirring for five minutes. The aqueous phase was separated and discarded. Three additional washes were made using 6.25 L of 1M NaCl. The organic phase was then dried over Na$_2$SO$_4$ and the methylene chloride stripped at 40° C. and −3 torr in a rotary evaporator to afford 629 g (∼90%) of a dark, viscous resin, $M_n$=696, $M_w$=1000, R=1.44. Examination of the infrared spectrum of the product showed no hydroxyl functionality in the resin. No inorganic salts could be detected by ion chromatography which indicated less than about 25 ppm was present. Upon thermal curing no void formation was observed.

EXAMPLE IV

Styrene/Propyl Terminated Tetraphenol Ethane (50% vinylbenzyl/50% Propyl). To a 2 L, 3 neck round bottom flask equipped with a stirring shaft, an additional funnel and a condenser was added 100.0 g TPE ($M_n$=274, $M_w$=711) (0.142 mol), 0.94 g BHT (0.00425 mol) and 475 ml N-methyl pyrollidinone (NMP). Upon dissolution of the TPE, 70.58 g vinylbenzyl chloride (VBC) (0.462 mol) was added and the vessel was flushed and placed under positive nitrogen pressure by means of a mineral oil bubbler. The solution was heated to 60° C. by a water bath and 30.22 g KOH (0.471 mol) dissolved in 70 ml of methanol were added dropwise over 30 minutes. The mixture was kept at 60° C. for an additional 2.5 hours. 50.4 ml 1-bromopropane (0.555 mol) was then added and 30.22 g KOH (0.471 mol) dissolved in 70 ml methanol was added dropwise over 30 minutes and the temperature maintained at 60° C. for an additional 3 hours. The mixture was cooled and 700 ml dichloromethane added. The mixture was washed with two 1.75 L-portions water and two 1.75 L-portions 1M NaCl (aq). The organic phase was dried over sodium sulfate and filtered through Celite. Solvent was removed by rotary evaporation up to 40° C. at 3 torr leaving an extremely viscous brown resin, 96% yield. GPC analysis found $M_n$=642, $M_w$=921, dispersity 1.44;

infrared analysis indicated no residual hydroxyl (<0.5%); ion chromatography analysis found: <4 ppm Cl—, <25 ppm Br—, <25 ppm $SO_4^{-2}$. Thermal curing produced a void free casting.

EXAMPLE V

Styrene/Propyl terminated m-cresol-dicyclopentadiene-formaldehyde condensate (STCDPF): To a 2-liter three necked round bottom flask fitted with a mechanical stirring shaft, a reflux condenser, and a pressure equalizing dropping funnel was charged 320 mL of 1-methyl-2-pyrollidinone, 0.68 g of BHT, 125.0 g of m-cresol-dicyclopentadiene-formaldehyde condensate ($M_n$=604, $M_w$=2970 and dispersity 4.92) and 82.34 g of vinylbenzylchloride. The reaction solution was brought to 60° C. with stirring with the aid of a water bath and then 80 mL of an ~9 molal solution of KOH in methanol was added dropwise over a 30 minute interval. The mixture was maintained at 60° C. with stirring for an additional 4.5 hours. 44.24 g of 1-bromopropane in 200 mL of 1-methyl-2-pyrollidinone was added to the reaction solution. 50 mL of ~9 molal KOH in methanol was then added dropwise over 30 minutes. The reaction was kept at 60° C. an additional 100 minutes and then allowed to cool to room temperature. 350 mL of toluene was added to the reaction mixture and the mixture transferred to a separatory funnel and washed with 3×900 mL of water. The organic phase was dried over sodium sulfate, slurried with celite and filtered through a glass frit, and the resin was isolated by removal of the solvent under vacuum ($M_n$=674, $M_w$=3040, dispersity 4.51). Infrared spectroscopy indicated the absence of hydroxyl functionality. Thermal curing produced a clean, void free casting.

What is claimed is:

1. A method of ether-capping oligomeric polyphenols with complete functionalization by both unsaturated and saturated ether moieties comprising reacting in the presence of a strong base at reaction conditions a solution of a polyphenol having at least four hydroxyl grams per molecule and both unsaturated and saturated phenolic hydroxyl-reactive halides in a polar aprotic solvent which maintains homogeneity of the reaction mixture with respect to all organic components therein, where said unsaturated halides contribute at least 40% of said ether moieties.

2. The method of claim 1 where the unsaturated ether moieties are derived from a phenolic hydroxyl-reactive halide selected from the group consisting of vinylbenzyl halides, benzyl halides, and allyl halides containing up to about 9 carbon atoms, and the saturated phenolic hydroxyl-reactive halide is an alkyl halide containing from 1 to 10 carbon atoms.

3. The method of claim 2 where at least 1 of the unsaturated phenolic hydroxyl-reactive halides is a vinylbenzyl halide.

4. The method of claim 1 where the polar aprotic solvent is selected from the group consisting of n-methylpyrrolidone, dimethylformamide, dimethylacetamide, hexamethylphosphoramide, and dimethylsulfoxide.

5. The method of claim 4 where the solvent is N-methylpyrrolidone.

6. The method of claim 1 where the base is an alkali metal alkoxide.

7. The method of claim 1 where the base is sodium methoxide.

8. The method of claim 1 where the base is an alkali metal hydroxide.

9. The method of claim 8 further characterized in that the reaction is performed in the presence of a drying agent.

10. The method of claim 1 where at least 50% of the ether moieties are unsaturated.

11. The method of claim 1 where the polyphenol is a mixture of oligomers whose weight-average molecular weight does not exceed 5,000.

12. A method of capping oligomeric phenols with complete functionalization with both unsaturated and saturated ether moieties comprising:

reacting in the presence of a strong base at reaction conditions a solution of a polyphenol having at least four hydroxyl groups per molecule and both unsaturated and saturated phenolic hydroxyl-reactive halides in a polar aprotic solvent in which all organic reactants and organic reaction products remain soluble throughout the course of reaction where the total halide is used in at least one equivalent amount and where said unsaturated halides contribute at least 40% of said ether moieties;

adding to the resulting reaction product mixture a water immiscible organic solvent, whose boiling point is no more than about 40° C. at 5 millimeters Hg pressure, in an amount sufficient to precipitate substantially all of the formed salts without insolubilizing the formed ether-capped oligomeric polyphenol;

washing the resultant mixture with water to remove the aprotic solvent and residual salts; and, recovering a salt-free solution of completely functionalized ether-capped oligomeric polyphenols as the organic phase.

13. The method of claim 12 where the unsaturated phenolic hydroxyl-reactive halide is selected from the group consisting of vinylbenzyl halides, benzyl halides, and allyl halides containing up to about 9 carbon atoms, and the saturated phenols hydroxyl-reactive halide is an alkyl halide containing from 1 to 10 carbon atoms.

14. The method of claim 13 where at least 1 of the unsaturated phenolic hydroxyl-reactive halides is a vinylbenzyl halide.

15. The method of claim 12 where the polar aprotic solvent is selected from the group consisting of n-methylpyrrolidone, dimethylformamide, dimethylacetamide, hexamethylphosphoramide, and dimethylsulfoxide.

16. The method of claim 15 where the solvent is N-methylpyrrolidone.

17. The method of claim 12 where the base is an alkali metal alkoxide.

18. The method of claim 12 where the base is sodium methoxide.

19. The method of claim 12 where the base is an alkali metal hydroxide.

20. The method of claim 19 further characterized in that the reaction is performed in the presence of a drying agent.

21. The method of claim 12 further characterized in that the precipitated salts are removed prior to washing the mixture with water.

22. The method of claim 12 where the organic solvent is an aromatic compound.

23. The method of claim 22 where the organic solvent is benzene, toluene, xylene, or any mixture thereof.

24. The method of claim 12 where the organic solvent is a haloalkane or haloalkene.

25. The method of claim 12 where at least 50% of the ether moieties are unsaturated.

26. The method of claim 12 where the polyphenol is a mixture of oligomers whose weight-average molecular weight does not exceed 5,000.

27. The method of claim 2 wherein said alkyl halide is bromopropane.

28. The method of claim 13 wherein said alkyl halide is bromopropane.

29. The method of claim 1 wherein the unsaturated phenolic hydroxyl-reactive halide is completely reacted with said polyphenol and thereafter unreacted hydroxyl groups are reacted with the saturated phenolic hydroxyl-reactive halide.

30. The method of claim 12 wherein the unsaturated phenolic hydroxyl-reactive halide is completely reacted with said polyphenol and thereafter interacted hydroxyl groups are reacted with the saturated phenolic hydroxyl-reactive halide.

* * * * *

UNITED STATES PATENT AND TRADEMARK OFFICE
CERTIFICATE OF CORRECTION

PATENT NO. : 4,871,831

DATED : October 3, 1989

INVENTOR(S) : Andrew M. Zweig and Jeffrey P. Conrad

It is certified that error appears in the above-identified patent and that said Letters Patent is hereby corrected as shown below:

Column 3, line 32: replace "is" with --in--;
Column 3, line 38: replace "and" with --an--.
Column 4, line 35: replace "later" with --latter--.
Column 11, line 42: replace "grams" with --groups--.
Column 12, line 41: replace "phenols" with --phenolic--.

Signed and Sealed this

Sixth Day of November, 1990

Attest:

HARRY F. MANBECK, JR.

Attesting Officer

Commissioner of Patents and Trademarks